United States Patent
Ellis et al.

(10) Patent No.: US 7,381,559 B2
(45) Date of Patent: Jun. 3, 2008

(54) FERMENTATION FLASK FOR CULTIVATING MICROORGANISMS

(75) Inventors: Samuel A. Ellis, San Diego, CA (US); Jeffrey L. Harlan, Corona, CA (US)

(73) Assignee: Scientific Plastic Products, Inc., Oceanside, CA (US)

( * ) Notice: Subject to any disclaimer, the term of this patent is extended or adjusted under 35 U.S.C. 154(b) by 0 days.

(21) Appl. No.: 10/864,219

(22) Filed: Jun. 9, 2004

(65) Prior Publication Data
US 2005/0277188 A1    Dec. 15, 2005

(51) Int. Cl.
    *C12M 1/24* (2006.01)
(52) U.S. Cl. ............... 435/288.2; 435/288.3; 435/297.1; 435/286.7; 435/304.2; 215/DIG. 1; 215/DIG. 8; 366/325.1
(58) Field of Classification Search ............ 366/130; 435/286.7, 288.1, 288.2, 297.1, 304.1, 304.2, 435/304.3, 305.1, 810; 215/DIG. 1, DIG. 8
    See application file for complete search history.

(56) References Cited

U.S. PATENT DOCUMENTS

| | | | |
|---|---|---|---|
| 3,870,602 A * | 3/1975 | Froman et al. | 435/304.3 |
| 3,933,965 A | 1/1976 | Gallone et al. | |
| 3,950,227 A * | 4/1976 | Efthymiou | 435/243 |
| 3,972,529 A | 8/1976 | McNeil | |
| 4,027,427 A | 6/1977 | Stoller et al. | |
| 4,197,287 A | 4/1980 | Piasio et al. | |
| 4,271,973 A | 6/1981 | Quagliaro et al. | |
| 4,665,035 A * | 5/1987 | Tunac | 435/304.2 |
| D306,262 S * | 2/1990 | Bit | D9/502 |
| 5,151,366 A * | 9/1992 | Serkes et al. | 435/299.2 |
| D332,050 S * | 12/1992 | Schmidt | D9/502 |
| 5,374,557 A | 12/1994 | Verma | |
| 5,395,006 A | 3/1995 | Verma | |

(Continued)

OTHER PUBLICATIONS

Mary Margaret G. Gozar, Saccharomyces crevisiae-Secreted Fusion Proteins Pfs25 and Pfs28 Ellicit Potent Plasmodium falciparum Transmission-Blocking Antibodies in Mice, Infection and Immunity, Jan. 1998, vol. 66, No. 1 p. 59-64, American Society for Microbiology.

(Continued)

*Primary Examiner*—David A Redding
(74) *Attorney, Agent, or Firm*—Stetina Brunda; Garred & Brucker

(57) ABSTRACT

A container is provided for cell growth by artificial cultivation of selected biological material in a growth liquid for use in an oscillating incubator. The container has a circular bottom with rounded corners joining a sidewall that is inclined at an angle toward a longitudinal axis of the container to define a container volume. The bottom has six equally spaced baffles extending inward from the corners and upward toward a large diameter opening of the container centered on the longitudinal axis. The baffles have a triangular cross-sectional shape with an included angle of about 28–40°, and a height measured parallel to the longitudinal axis of about 15–25% of the usable container volume. The baffles end before the longitudinal axis. The container and baffles are blow molded of a polymer suitable for blow molding. An air permeable filter is placed over the container opening, with the filter having an adhesive on one side to stick to the container. A finger tab on the periphery of the filter helps position and remove the filter.

48 Claims, 4 Drawing Sheets

U.S. PATENT DOCUMENTS

D414,112 S    * 9/1999  Waggaman et al. .......... D9/520
D453,003 S    * 1/2002  Rashid ....................... D9/502
D487,564 S    * 3/2004  Beck et al. .................. D9/520
2002/0113013 A1  8/2002  Long et al.

OTHER PUBLICATIONS

Sigma Catalog, Techware Equipment, Books and Supplies, pp. 2356 & 2357, 2000-2001.

* cited by examiner

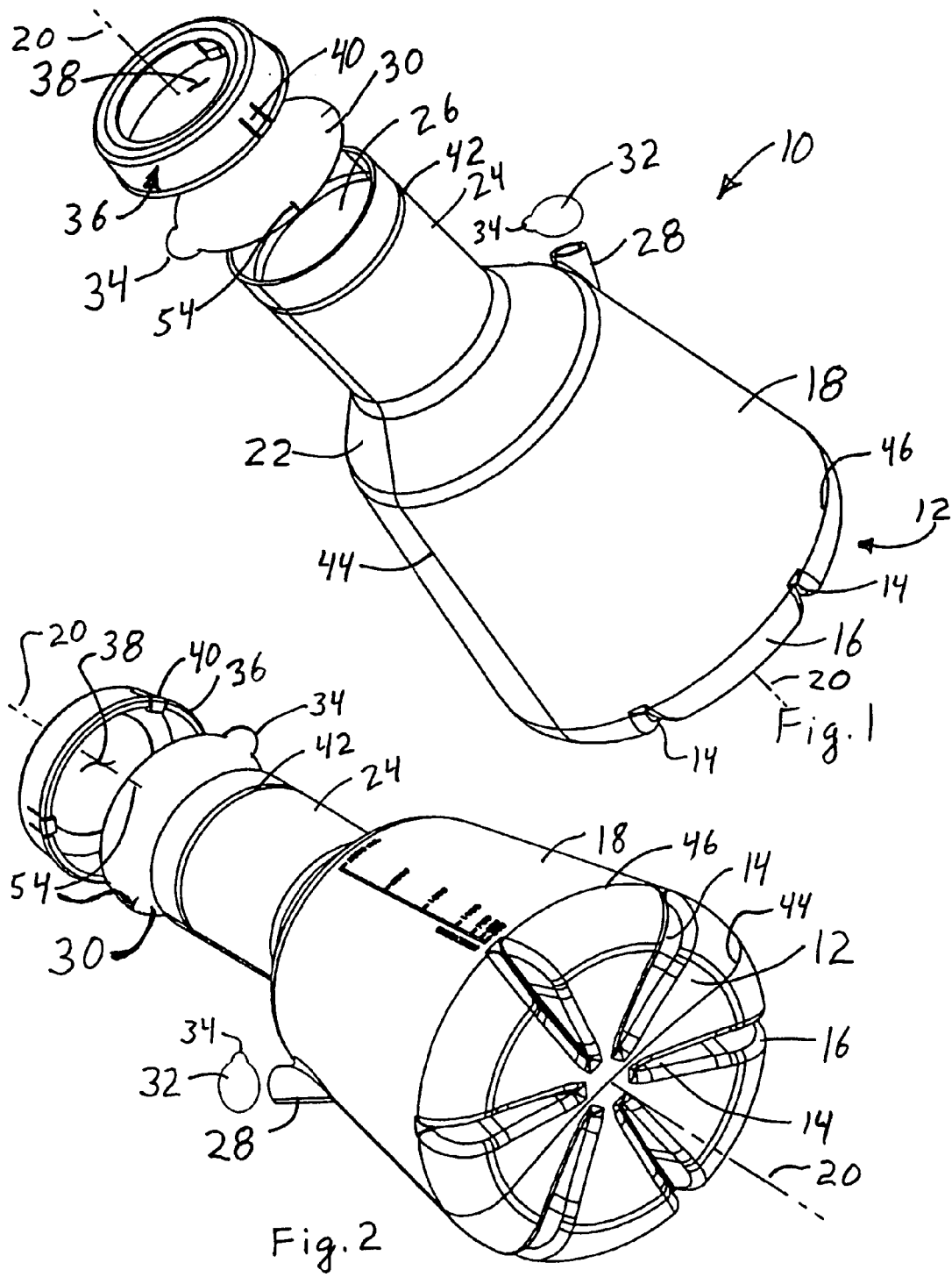

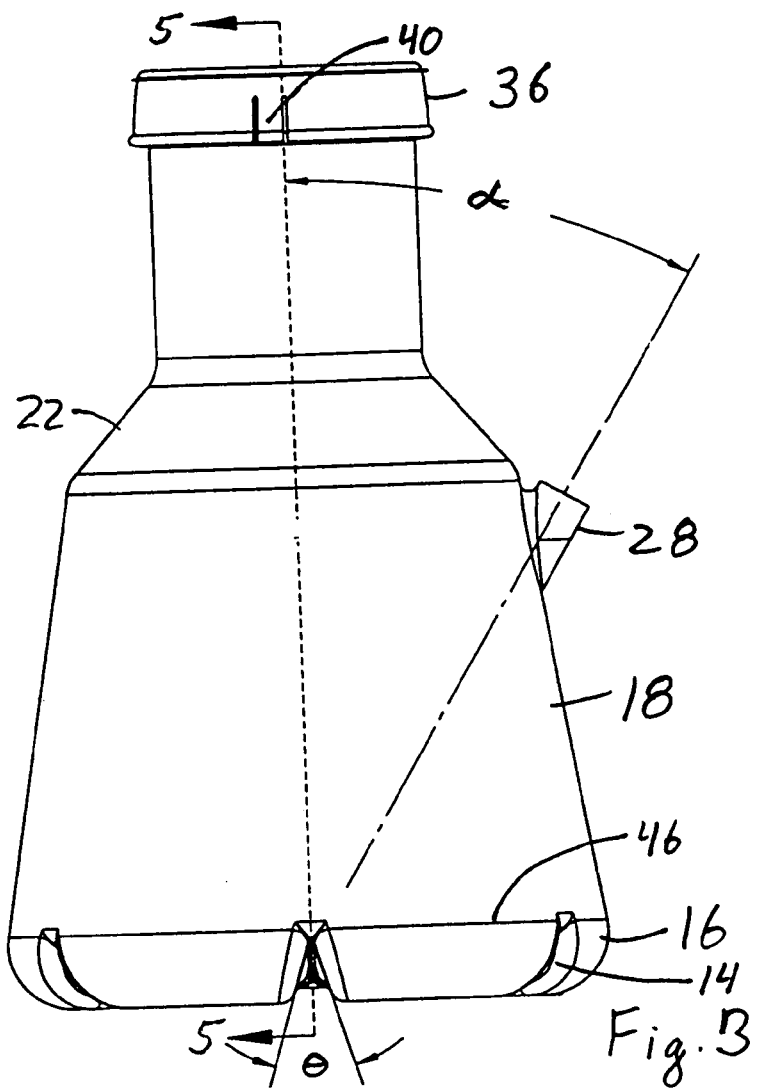
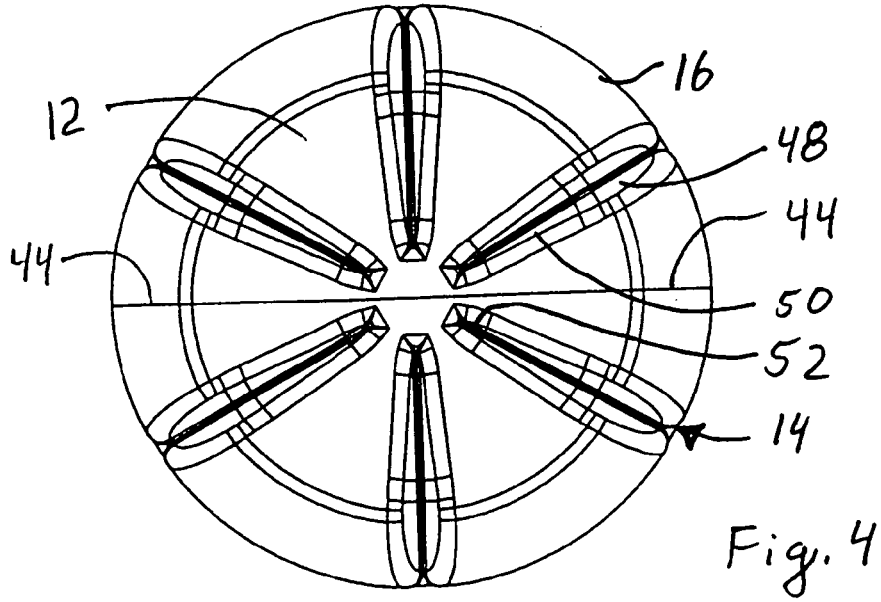
Fig. 3
Fig. 4

FERMENTATION FLASK FOR CULTIVATING MICROORGANISMS

BACKGROUND OF THE INVENTION

This invention relates to flasks or containers and systems used for aerobic fermentation used to cultivate the aerobic growth of microorganisms, cell lines or other biological organisms.

For a variety of biotechnology applications there is a need to take a few biological organisms and as quickly as possible, multiply or grow them into significantly larger numbers of organisms. The biological growth usually increases with the oxygen level.

One common method of cultivating biological organisms is to place them in a flask in a liquid medium, and then oscillate the flask at a predetermined rate in an enclosed incubator. This approach can use a flask disclosed in a patent to Tunac, U.S. Pat. No. 4,665,035, which flask uses specific patterns of baffles on the bottom and neck of the flask. But Tunac's use of these baffles, including the internal baffles to inhibit the fluid from splashing out of the flask, has significant disadvantages. The cost of making the Tunac flasks is high enough that they must be reused. Unfortunately, reuse requires cleaning the flasks and filters in an autoclave and despite such cleaning it is not uncommon to have sufficient contaminants remain that reuse of the flask contaminates the samples cultivated in the reused flask. There is thus a need for an efficient flask that overcomes these deficiencies.

Further, the goal of cultivation is to produce as large an increase in the biological organisms as possible in as little time as possible. The use of the prior art containers, such as Tunac, often produce inconsistent growth rates, in part due to residual contamination arising from reuse. There is thus a need for a container that produces an increased growth rate of the biological organisms, consistently, and preferably while reducing the risk of contamination.

The prior art containers allow air to enter the container, and many containers filter the air. For example, Tunac describes a complex ribbed cap and filter to help diffuse oxygen in the flask. But the cap and filter in Tunic's container are expensive to make, and are thus reused, resulting in a risk of contamination and high operating costs. There is thus a need for an improved cap design.

The prior art containers have openings at the top of the containers and laboratory personnel often insert pipettes through these openings to gather samples and add contents from the containers at various stages of cultivating the biological organisms in the containers. As the containers become larger longer pipettes are needed, and laboratory personnel sometimes tilt the containers and spill everything out in using the pipettes. Further, removing and reattaching the caps to access the containers sometimes contaminates the caps. There is thus a need for an improved way to allow sampling of and addition to the contents of the containers while reducing contamination.

BRIEF SUMMARY

A blow-molded, disposable flask is provided to reduce costs and contamination. The flask has a bottom with specially located and shaped baffles which increase the agitation of the biological material and cause a surprisingly consistent and increased growth of the material. The flask preferably has a bottom with rounded peripheral edges joining a conical sidewall that tapers inward slightly until it reaches a height of about the same as the diameter of the bottom. A short, inwardly tapered transition area joins a neck to the bottom wall, with the neck having a diameter that is about half the diameter of the bottom. The neck ends in an opening that is covered by a circular sheet of disposable filter material which preferably has adhesive on one side to removably fasten the filter over the opening and to the neck of the flask. The disposable filter allows ample oxygen access while providing a reduction in the risk of contamination and reducing costs. A finger tab extending from the filter allows easy attachment and removal of the filter without touching the surface exposed to the inside of the flask. A ring-shaped cap with an open top can be optionally used to hold or to help hold the filter over the opening. A pipette access port can optionally be formed in the bottom or transition portion of the flask. The access port is preferably located about 6 inches or less from the center of the bottom of the flask in order to accommodate a wider range of pipette sizes than previously usable while reducing the risk of contamination, and spilling of the contents. The pipette port can be covered by a smaller version of the filter covering the flask opening to further reduce the risk of contamination.

BRIEF DESCRIPTION OF THE DRAWINGS

These and other advantages and features of this invention will be better understood by reference to the following drawings, in which like numbers refer to like parts throughout, and in which:

FIG. 1 is a perspective view of a container of this invention with a holder cap and side port;

FIG. 2 is a perspective view of the container of FIG. 1;

FIG. 3 is a side view of the container of FIG. 1;

FIG. 4 is a bottom view of the container of FIG. 3;

DETAILED DESCRIPTION

Figure 5:
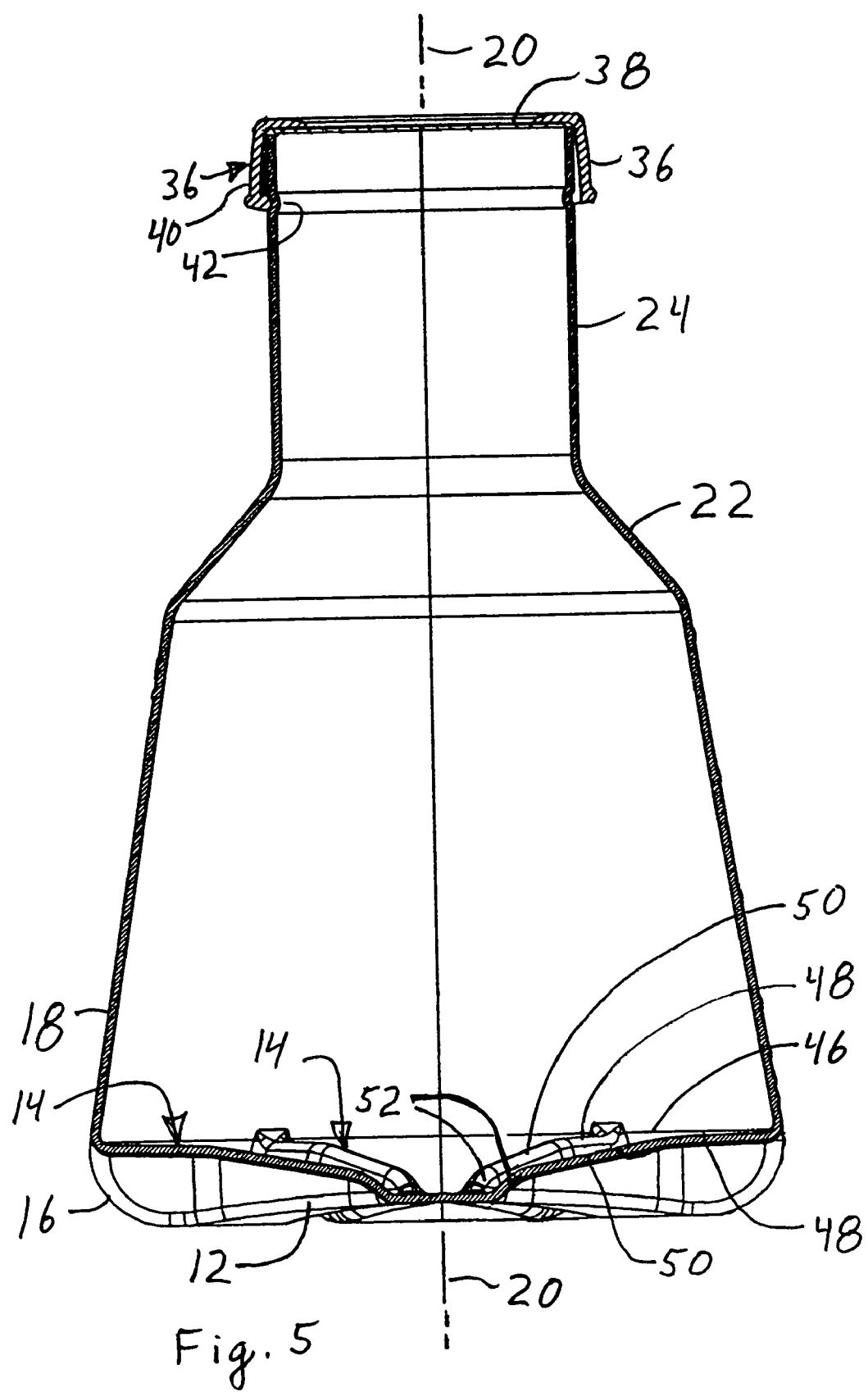
FIG. 5 is a sectional view taken along 5—5 of FIG. 3.

Referring to FIGS. 1–5, a container 10 is provided having a bottom 12 with a plurality of baffles 14 formed in the bottom. The bottom 12 has a curved peripheral corner 16 which joins sidewall 18 that angle inward toward longitudinal axis 20 to form a conical structure. A transition area 22 joins the sidewalls to an elongated neck 24 having an opening 26 in a distal end of the neck. An access port 28 is formed in the side of the container, advantageously in either the transition area 22 or sidewall 18. A first filter 30 covers the opening and a second filter 32 optionally covers the access port, each filter having a finger tab 34 to facilitate handling and removal of the filter. A cap 36 optionally holds the first filter 30 onto the neck 24. The cap 36 preferably comprises an annular flange with an opening 38 about as large as the opening 26 in the neck 24. Resilient locking tabs 40 are cut or formed in the flange of the cap 36, with distal ends of the locking tabs 40 engaging an annular recess or protrusion 42 encircling the neck 24 to releasably hold the cap to the neck of the container 10. The container 10 is preferably blow molded using a three-part mold, and if so it will typically result in two opposing vertical mold lines 44 on opposite sides of the sidewall 18 and neck 24, and a horizontal mold line 46 at the juncture of the corners 16 and the sidewall 18.

The use of the container 10 is described as follows. Following blow molding or other formation of the container 10, it is cleaned if needed and then placed in a clean bag and the bag is sealed, with heat sealing being commonly used. The bags are typically made of plastic. The filter(s) 30, 32 can be placed inside the same bag as container 10, but are preferably placed in separate bags that are sealed. If a cap(s) 36 is used, it can be placed in the same bag loosely, or covering the container opening 26, or placed in a separately sealed bag. The same applies to any cap over the port 28. The sealed bags and their contents are then sterilized, typically by irradiation, and commonly by electron beam irradiation or cobalt radiation. The sterilization is a laboratory level of sterilization rather than a medical level of sterilization. The sealed and sterilized bags are then packaged in one or more boxes and shipped to a distributor or user.

A user unpacks the box and takes the container, removes it from the protective or sealing bag, removes any cap 36 that may or may not be covering the opening 26, and may then directly place any biological material in the container 10. Typically the biological material is mixed with fluid or liquid growth medium, often water, in a ratio of about one part biological material to about nine parts fluid. This mixture will be referred to as the biological media. The filter 30 and/or cap 36 is then removed from its own sealed bag, as needed, and placed over the opening 26 of the container. The same applies for any cap or filter 32 for use in covering the port 28. The container 10 with the biological media inside it and appropriate caps 36 or filters 30, 32 are then placed in a commercially available incubator which completely encloses the container, which maintains a predetermined temperature, and which oscillates the container at selectable speeds. The incubator temperatures are typically under 150° F. but can be varied according to the biological material used. Oscillations of about 300 rpm or less for periods of an hour or more are common, but the incubators can operate at much greater speeds for longer or shorter times. The incubators typically hold the bottom sides of the container and oscillate the container 10 about a circular path with a radius of about 1.0 inch, usually about longitudinal axis 20. The user may remove the container from the incubator and check the biological media, in which case one or both of the filters 30 or 32 are removed. The filter can be discarded and a new filter 30 or 32 removed from a separate sterile bag and used to reseal the opening 26 or port 28, whereupon the container is replaced in the incubator for further growth of the biological material. When the growth is completed, the biological media is removed from the container through opening 26 and the container 10 and any filters 30, 32 and cap 36 are discarded.

The size of the container 10 is preferably selected so that when the container is setting flat on a support the level of the biological media measured along axis 20 is advantageously is about the same as or slightly greater than the maximum height of the baffles 14, although levels as low as ½–¾ the baffle height are believed to offer increased growth over the prior art. Levels about 0.8 to about 1.5 times the average height of the middle portion 50 of the baffle 14 (described below) are believed advantageous.

The usable volume of containers 10 is typically about five times the volume of the biological media placed in the container for cultivation or growth. Thus, a 500 ml sample is typically placed in a 2.5 liter container, and the 2.5 liter container is considered the usable container volume, even though the container could contain more fluid. The usable volume of the containers 10 is typically smaller than the actual volume of the containers, with the usable volume being defined within the sidewall 18, and typically not including more distal portions of the container. Further, the actual volume within the sidewall 18 is also slightly larger than the usable volume as reflected by fluid level markings on the sides of the containers. This is reflected by the fluid level markings on the sides of the containers 10 which terminate below the juncture of the sidewall 18 with the neck 24 or the transition 22. The fluid level markings may be accurate for flasks having flat bottoms, but these markings are not accurate for contoured bottoms like bottom 12 that curve and that have baffles 14 in them, such that the fluid level may vary by 50 ml. These variations are accepted in the trade which uses these flasks to culture biological media. Thus, as used herein, the usable volume refers to the intended usable volume of the container even though that actual volume within the sidewall 18 is larger and even though the actual volume as reflected by the fluid level markings on the side of the container may be larger or smaller than the usable volume. The baffles 14 preferably have a height that corresponds to about 15–25% of the usable volume.

The height of the baffles 14 at the corners 16 preferably does not come up to this normal ⅕ full level of the biological media, and the baffles are advantageously slightly below that level, and preferably about 80% the height of that level when measured along longitudinal axis 20, although they could be about 25% higher than that level.

The oscillation causes the biological media to splash over the baffles 14 and expose the media to oxygen which increases growth of the biological material in the fluid comprising the media. As needed the port 28 can be used to allow a pipette to access the biological media or it can allow the addition of further biological material to the container 10. When incubation of the biological media has reached a desired stage, the container 10 is removed from the incubator, the filter 30 and/or cap 36 removed, and the biological media is emptied from the container. The container 10 is then discarded.

Preliminary testing has indicated a surprising increase in growth of biological material compared to prior art flasks. The increase varies with the biological materials but an increase of over 20% is indicated by preliminary experiments, on a fairly consistent, batch-to-batch basis. Preliminary indications are that the increase in growth seems to be fairly independent of the oscillation rate. Further, the amount of agitation of the biological media by the baffles 14 also seems to be fairly uniform over oscillation rates of under about 1,500 rpm. The ability to acquire the blow-molded container 10 at a low enough price that the container can be discarded significantly reduces the risk of contamination from the container.

In more detail, the baffles 14 have a generally triangular cross-sectional shape that changes size along the length of the baffle. The baffles 14 extend from the bottom 12 inward into the container 10, and extend from the corners 16 inward toward central axis 20. The baffles 14 have a larger axial height and circumferential width at the peripheral corner 16 of the container where the bottom 12 joins the sidewall 18. The baffles 14 extend radially inward toward central axis 20 and narrow in circumferential width and axial height as the baffles approach that axis. Preferably there are six baffles 14, equally spaced at about 60° apart. As seen in FIG. 3, the baffles 14 have a triangular cross section with side-walls inclined at an angle of about 17° to the vertical, where longitudinal axis 20 represents the vertical axis. For purposes of description, the horizontal plane is orthogonal to the vertical axis, and the bottom 12 rests on the horizontal plane. The sidewalls of the baffles 14 thus form an apex with an included angle $\theta$ (FIG. 3) of about 34°. Preferably this angle is fairly constant along the length of the baffles 14 as they extend from the corners 16 toward the center axis 20. Angles of about 28–40° for the included angle θ are also believed suitable but have not been tested.

It is believed possible to have one side of each baffle 14 be generally perpendicular to the bottom, or generally parallel to a plane through the longitudinal axis 20. The agitation causes the biological media to flow up the leading inclined surface of a baffle 14 and then splash over the apex of the baffle. The biological media flows up the leading side and flows down the trailing side. Having an inclined trailing side on the baffle reduces some of the agitation as the media flows down the trailing side rather than splashing. Thus, for example, it is believed advantageous to have the leading side of the baffle inclined at an angle of about 17°, and to have the trailing side less inclined and preferably perpendicular. When the baffles are blow molded it is easier to have them symmetric and it is more difficult to form a perpendicular side on the trailing side. Thus, the perpendicular side may have a slight inclination to it, preferably less than about 5° from the vertical. Of course having different angles on the leading and trailing sides also requires knowing in advance the direction in which the container 10 is oscillated so the correct angles can be placed on the correct leading or trailing side of the baffles 14. If the flask 10 can be oscillated in either clockwise or counterclockwise directions, then inclined surfaces on each side of the baffle are preferred. If the container 10 is oscillated in the clockwise direction, then the inclined leading side is on the clockwise side of the baffles and the more steeply inclined, trailing side of the baffle is on the counterclockwise side of the baffle. If the container 10 is oscillated in the counterclockwise direction, the leading side is on the counterclockwise side, and the trailing side is on the clockwise side of the baffle.

Referring to FIG. 4, the baffles 14 are symmetric about a diameter of the container 10 passing through any two baffles, and are illustrated as symmetric about mold line 44 which passes equally between two adjacent baffles. Each baffle 14 is preferably substantially the same. Referring to FIG. 5, as the baffles 14 extend toward the center they narrow in axial height, with the apex of the inclined sidewalls of each baffle preferably approximating a curved line approximating a quadrant of an ellipse where the ellipse is inclined at about 8–15°. The interior ends of the baffles 14 preferably do not abut each other, and preferably merge into the bottom 12 away from the center 20 at a radius of about ⅙ to ⅐ the diameter of the bottom 12. The corners 16 preferably are rounded, and advantageously have a radius of about 0.4–0.6 inches, and preferably have a radius of about 0.5 inches, although the radius will vary with the size of the container, being a larger radius with a larger container.

At the corner 16, the baffles 14 are advantageously about ½ to 1 inch high, and preferably about ¾ inches high relative to a surface on which the container bottom 12 rests, when measured parallel to the axis 20. This height applies regardless of the diameter of the container 10, up to diameters of about at least 15 inches. The curved surface of the apex of the baffles 14 is preferably approximated by straight segments in order to facilitate blow molding. The first segment 48 is the radially outermost segment and has axial height of the baffle 14 tapering toward the bottom 12 at an angle of about 2° below the horizontal for a distance of about ⅓ the radius of the bottom 12. The second or middle segment 50 has the axial height of the baffles 14 taper at an angle of about 11° below the horizontal for a distance of about ½ of the radius of the bottom 12. The third or distal segment 52, which is closest to the center axis 20 and forms the toe of the baffle, tapers toward the bottom 12 at an angle of about 45 degrees below the horizontal for a distance of less than about ⅙ the radius of the bottom and closer to 1/12 of that radius. The bottom 12 between baffles 14 is not horizontal, but instead the middle ⅔ to ⅞ of the bottom 12 curves toward the top of the container 10 a distance of about 0.2–0.4 inches at a constant radius of curvature located on axis 20. The bottom 12 is thus slightly curved with the apex of the curve at the longitudinal axis 20.

The sidewall 18 extends from the corners 16 to the transition 22. The sidewalls are preferably, but optionally, inclined inward, toward axis 20, at an angle of about 10–20° from the vertical. The angle can vary but is preferably selected to cause fluid in the container to easily flow back along the sidewall 18 to the bottom. The transition 22 joins the larger diameter sidewall 18 with the smaller diameter neck 24. The transition is preferably short in axial length along axis 20, and is inclined toward the axis 20 at an angle of about 45–55° to the horizontal. The neck 24 is cylindrical, preferably with a diameter about twice the diameter of the bottom 12.

Adjacent the distal end of the neck 24 is preferably, but optionally, an annular recess 42 into which the distal end of the resilient lock 40 fits to form a releasable snap-lock if a cap is used. The recess 42 could be a rim or protruding flange which also engages the distal end of the lock 40. The cap 36 has a depending annular flange with a plurality of locking tabs 40 formed therein. Three locking tabs 40 are shown, each with a distal end configured to releasably engage the recess or flange 42. Various ways of releasably fastening the cap 36 to the neck 24 can be used, including threads, partial threads, and other forms of snap-locks and releasable locks.

Referring to FIGS. 1–2, the opening 38 in cap 36 is preferably defined by a horizontal rim of the cap. The opening 38 is preferably circular and is preferably as large as possible to allow the maximum volume of air to pass through the opening. The filter 30 is interposed between the edges of the neck 42 and the cap 36, and extends over the opening 26 and across the opening 38 and cap 36 are (when the opening 38 and cap 36 are present). The filter 30 is preferably about the same diameter as the outer portion of the neck 24 when the cap 36 is used. But the filter 30 could be larger and folded along the sides of the neck 24. For shipment of the container 10, the opening 38 can be blocked by a removable disk in order to protect the filter 30 and interior of the container 10 from contamination. This is useful for shipping and also for potential storage of the biological media. This removable disk blocking the opening 38 can be separate, or formed as a punch-out portion of the cap 36. In a further embodiment of the cap 36, there is no opening 38 and the cap is merely a protective cap to reduce contamination of the container 10, with the cap being removed to place biological material in the container, and then the cap is discarded after the filter 30 is placed over the opening 26. Further, the cap 36 could be made with a solid top which would be suitable for shipping and storage, but not desirable for growing the biological media because it would limit air flow to the biological media.

The filter 30 preferably comprises a porous, thin sheet of air-permeable material. The filter 30 can have a diameter large enough to engage the edge of the neck 24 defining opening 26, but preferably extends over a portion of the neck 24. The upper rim of cap 36 can hold the filter 30 to the container 10, or the side flange can hold the filter to the container. The filter 30 is preferably thin in order to allow air to easily pass into and out of the container 10, but is preferably thick enough to be self-supporting so it does not sag and fall into the neck 24. A filter 30 a few hundredths of an inch thick is believed suitable.

Preferably there is no cap 36 and the filter 30 has a releasable adhesive on one side to fasten the filter 30 over the opening 26 of the neck 24 and fasten the filter to the neck 24. A 1530L tape made by 3M is believed suitable for the filter 30. If no cap is used, the filter 30 is preferably about 15–30% larger in diameter than is the neck 24 defining the opening 26, with a portion of the filter abutting and releasably adhering to the sides of the neck 24.

The filters 30, 32 can take various forms. The filters preferably comprise air-permeable tape of the type that is used on band-aids. The general specification for the 1530L tape is a rayon nonwoven backing coated on one side with a hypoallergenic pressure-sensitive acrylate adhesive. Such a tape is about 0.006 inches thick. Thicker tapes could be used. The tape is supplied on a polyethylene coated paper liner with silicone coated on one side, with the paper about 0.005 inches thick. The adhesive allows easy fastening and removal of the tape which is sufficiently thin and air permeable to function as a filter that prevents undesirable contaminants from passing in or out of the filter, while allowing air permeability. If desired, a thin filter material could be backed by a similar releasable adhesive.

The filter 32 used on the port 28 is preferably air permeable, but need not be so. The filter 32 is more likely to be splashed with biological media than is the filter 30, and thus using a waterproof material instead of an air permeable filter 32 has advantages for reducing contamination. The filters 30, 32 are preferably each packaged in separately sealed and sterilized packages so they can be provided separate from the container 10, but two filters 30, 32 could be in the same laboratory-sterile package. Depending on the number of times the contents of the container are accessed through opening 26 or port 28, the number of filters 30, 32 that are used can vary. The filters are preferably discarded once removed in order to avoid possible contamination, so separately packaged filters are desirable. The releasable adhesive and finger tabs 34 make the removal and discarding of these filters a much easier and contamination free task.

One or more slits 54 can be extend from the periphery of the filter 30 toward the center of the filter so that the portions between the slits can more easily fold flat against the curved sides of the neck. Preferably the filter 30 is circular and the slits are radial, and advantageously there are three to six slits 54. The slits 54 preferably extend inward a distance sufficient to form a central portion which covers the opening 26 without having the slits extend into the opening by more than a short distance, say ⅛ inch or so. The slits 54 are optional.

There is preferably, but optionally, a finger tab 34 sufficiently large to allow a person to grab it and remove the adhesively backed filter 30. The tab 30 also allows easy placement of the filter 30 over the opening 26. The tab 26 preferably has no adhesive on it. The adhesive surface on filter 30 is preferably placed against a backing (not shown) to protect the adhesive until used. The backing is peeled off before use and discarded. Such backing sheets are known. If a backing material is used, then the filter 30 can be very thin, and can even be thin enough that it can sag into the opening 26, with the backing and adhesive surface releasably adhering to the neck 24 prevent the filter from falling into the container 10. Advantageously, the filters are thick enough to not substantially deform under their own weight so they can be positioned by use of the tab 34. As mentioned above, the 1530L tape is believed suitable for the filters 30, 32.

The opening 26 is a large opening, in that it is advantageously at least ⅓ the diameter of the bottom, and preferably about half the diameter of the bottom 12 or larger. If the opening 26 is too small, then oxygen flow to the biological material is reduced and growth is reduced.

Referring to FIGS. 1–5, the port 28 preferably comprises an opening that is small relative to the opening 26 of the container 10. The port 28 is sized just large enough to comfortably allow passage of a pipette (not shown) which is used to sample the biological material being cultured or grown in the container 10 or to inject materials into the container. Preferably the port 28 is located so that a pipette (not shown) can be inserted through the port 28 and reach the inside, bottom-center of the container 10, which corresponds to the space defined by the interior ends of the baffles 14. Advantageously the distance from the outer or distal end of port 28 to the intersection of axis 20 with the bottom 12, is about 5–7 inches, and preferably it is about 6 inches. That spacing allows shorter pipettes to be used. If the container 10 is small enough that the end of neck 24 is about 5–6 inches from the intersection of the axis 20 and bottom 12, then the port 28 is advantageously omitted. But the port 28 can be used on such small containers, or smaller ones. The port 28 can be omitted on any sized container as the port is optional.

Preferably, but optionally, the walls defining the access port 28 are not perpendicular to the wall of the container 10 on which the port is located, but rather the port 28 is inclined at an angle sufficient to allow a pipette inserted through the port to reach the intersection of the axis 20 with the bottom 12. Advantageously the port 28 is at an angle $\alpha$ (FIG. 3) of about 30–40° from the vertical, but the orientation can vary. A port 28 about ⅝ inch to one inch in diameter is believed suitable, but he size can vary as desired. The port 28 preferably sticks out enough from the sidewall 18 or the transition portion 22 for the cap 36 or filter 32 to removably fasten to the port.

If the port 28 is used, then preferably it is covered by a removable cap or filter. Advantageously the cover takes the form of a filter 32, and preferably that filter comprises a smaller version of the filter 30. If desired, a smaller version of the cap 36 could be adapted for the port 28, with the walls of the port having a recess or flange analogous to that found in recess 42 in the neck 24. Rather than repeat the descriptions, the prior descriptions and variations of cap 36 and filter 30 and recess 42 are simply referred to here and are not repeated in full.

The container 10 can be made of various materials as long as they are biologically compatible with the biological material to be grown in the container. Advantageously the container is molded of a polymer material, including but not limited to such materials as polyethylene (including HDPE or high density polyethylene), polypropylene, polyethylene-tri-glycol (PETG), or polycarbonate. A wall thickness of about 0.080–0.090 inches is believed suitable. Preferably the container is blow molded, and with the above wall thickness that may result in the baffles 14 being thinner. Preferably, when blow molded of polypropylene the thinnest the various walls get is about 0.025 inches thick, and that includes the bottom 12, baffles 14, corners 16, sidewall 18, transition 22, neck 24 and port 28. But the thickness will vary with the size of the container 10 and the material and method used for form the container. Injection molding could be used, but it is very desirable to make the container as inexpensive as possible, so blow molding the container 10 using a material that lends itself to blow molding thin walls, is desirable.

For a container 10 having a bottom 12 about 6–7 inches in diameter, the baffles 14 are about ¾ inches high at the corners 16, and the inner ends of the baffles are spaced about 0.5 inches apart from the diametrically opposing end. Such a container 10 has the transition 22 beginning about six inches from the bottom corner 16 which rests upon the surface supporting the container. The neck 24 has an outer diameter of about 3 inches, and a length of about 4 inches. The container 10 thus has a height of about 11 inches measured along axis 20, with the filter 30 having a diameter of about 3 inches if it fits within cap 36, and a diameter of about 3–4 inches, and preferably about 3.8 inches, if the cap is not used.

Figure 7:
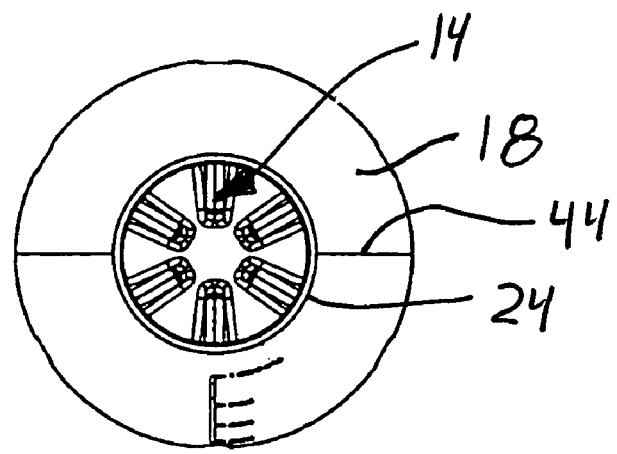
FIG. 7 is a bottom view of the container of FIG. 6.
Figure 6:
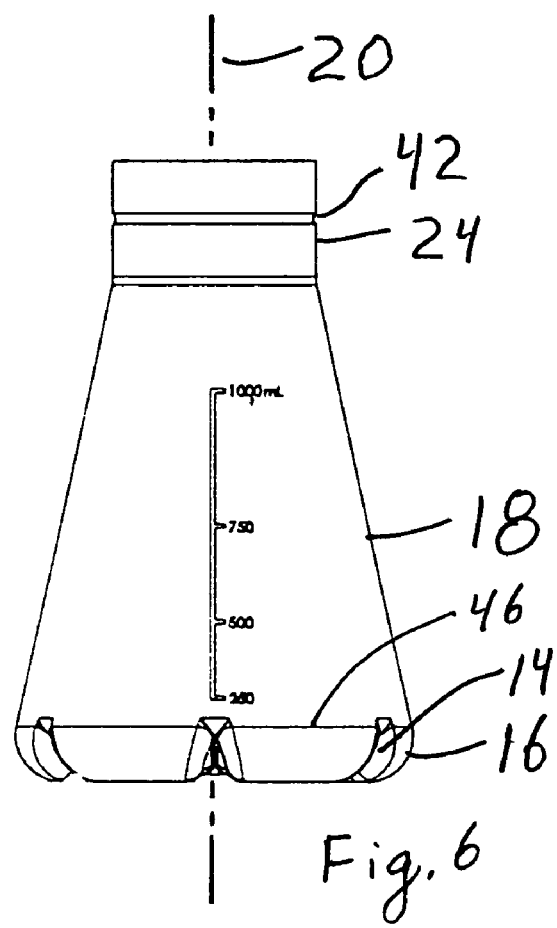
FIG. 6 is a side view of a further embodiment of the container of FIG. 1.

Referring to FIGS. 6–7, a further embodiment is described which has no transition area 22 and no port 28. This embodiment is preferably used with a smaller volume of container 10, volumes up to about 1000 ml, but it could be used with larger containers. As indicated by the markings on the side of the container, the total volume of the container is greater than the effective volume used for culturing biological materials, and that volume is measured by the volume below the end of the sidewall 18, before the juncture with any neck 24 or transition 22. The depicted container 10 has a bottom 12 with a maximum diameter of about five inches adjacent the corners 16, and a height of about five inches to the opening 26, with a neck of about 2.5 inches in diameter. There is no transition area 22 in these smaller containers. The transition area 22 is useful in the larger containers in order to reduce the height of the container and make it easier to handle and to fit in then existing incubators.

The above embodiments show six baffles 14. It is believed possible to use 4–8 baffles 14 and still improve the growth rate of the biological media. Preferably the number of baffles 14 is an even number, and the baffles are evenly spaced around the bottom 12.

The surprising increase in growth rates of biological materials makes the container 10 very desirable. The ability to make the container 10 by blow-molding offers significant advantages in avoiding contamination. The use of the adhesive filters 30, 32 offers further advantages in avoiding contamination as the filters can be entirely replaced at low cost if they are removed during incubation. The use of the pipette port 28 offers a way to avoid removing the main filter 30 and by locating the port 28 as described a technician can use any of a variety of common lengths of pipettes and need not worry about contaminating the container by reaching down the neck with a short pipette. The blow molding provides all these advantages at a lower cost.

The container 10 is formed by a three-part mold, using blow molding. The bottom 12, baffles 14 and corner 16 are formed by a first mold part, which leaves horizontal mold 46 line. Two other mold parts form half of the remainder of the container 10, with each mold part forming half of sidewall 18, transition 22 (if present), and neck 24, with the side mold parts abutting along vertical mold line 44. After blow molding, the three parts are pulled apart to allow removal of the blow-molded container 10.

The blow molding allows the inexpensive fabrication of a container 10 of relative thin walls. The blow molding allows the bottom 12 to vary in contour to form the baffles 14 that agitate the biological media. The prior art Tunac container is believed to use sonic welding to fasten solid baffles to the bottom of the Tunac flask. But as the lower surface of the baffles increases in size it is believed to become more difficult to get a weld line that avoid small cavities in which contaminants can accumulate. The blow molding which contours the bottom allows formation of baffles 14 having larger cross-sectional shapes and sizes on the lower surface, while avoiding the formation of small cavities that can accumulate contaminants.

The formation of a container 10 with baffles shaped or formed by and integral with a thin-walled bottom is believed new and very advantageous. The use of a blow-molded bottom with a contoured surface to form baffles that increase the agitation of the biological media is believed both new and very advantageous.

The baffles 14 are preferably radial and symmetric, with a triangular cross-sectional shape. More accurately the bottom 12 forms two inclined sides which extend toward the opening 26 and join at an apex, with the apex being curved from the sidewall 18 toward the bottom 12. The apex could be straight for the entire length of the baffle 14, and is straight for the three segments 48, 50 and 52 that approximate the previously described curve of the apex. But the apex could also curve when viewed parallel to the longitudinal axis 20, which places the curve in the horizontal plane. Such curves are shown in the baffle shapes disclosed in the patent to Tunac, U.S. Pat. No. 4,665,035, the complete contents of which are incorporated by reference. Preferably the baffle shapes of Tunac are modified to have the dimensions described herein, and are formed using the thin walls of the bottom rather than fastening solid baffles to a previously formed bottom as in Tunac.

The two opposing sides of each baffle 14 are described above as being generally flat or straight. It is believed possible that the sides could be slightly curved as they extend from the bottom 12 to the apex. Preferably the leading side of the baffle 14 is slightly concave, so as to cause the biological media to flow higher and splash more. The trailing side of each baffle is preferably straight, but could be either convex or concave. If the leading side is straight or convex, the trailing side can be concave in order to cause splashing. Slight curvatures are believed desirable so that the maximum deviation from the bottom 12 to the apex of the baffle does not deviate more than about 0.2–0.3 inches from a straight line joining the apex and bottom where the baffle 12 begins, with deviations of less than about 0.1 inches being believed preferable. But various curvatures can be used, especially as if the size of the baffles becomes larger.

Each baffle 14 is preferably identical, but it is possible to vary the shape of the baffles. It is believed advantageous to have the baffle shapes cyclical and symmetric. Thus, for example, if there are six baffles the leading side of every other (e.g., odd numbered) baffle may be concave and the trailing side the other baffles (e.g., the even numbered baffles) may be concave, with the remaining surfaces being either all straight, all convex, or alternating.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The above description is given by way of example, and not limitation. Given the above disclosure, one skilled in the art could devise variations that are within the scope and spirit of the invention, including various ways of sealing the openings 26, 28, and various ways of fastening the cap 36 to the container 10. Further, the various features of this invention can be used alone, or in varying combinations with each other and are not intended to be limited to the specific combination described herein. Thus, the invention is not to be limited by the illustrated embodiments but is to be defined by the following claims when read in the broadest reasonable manner to preserve the validity of the claims.

What is claimed is:

1. A container for cell growth by artificial cultivation of selected biological material in a growth liquid for use in an oscillating incubator, comprising:
the container having a circular bottom with rounded corners joining a sidewall that is inclined at an angle toward a longitudinal axis of the container to define a usable container volume, the bottom having a diameter with six equally spaced baffles extending inward from the corners toward the longitudinal axis and upward toward a large diameter opening of the container centered on the longitudinal axis, the baffles having a triangular cross-sectional shape with an apex having an included angle of about 28–40°, and a height measured parallel to the longitudinal axis of about 15–25% of the usable container volume, the baffles ending before the longitudinal axis but extending to within a distance from that axis that is at least about 1/6 the diameter of the bottom, the container and baffles being blow molded of a polymer suitable for blow molding.

2. The container of claim 1, wherein the baffles extend radially inward and end before the longitudinal axis at a distance of about 1/6 to 1/7 the diameter of the bottom.

3. The container of claim 1, further comprising a pipette port formed in the sidewall.

4. The container of claim 3, wherein the port is within about six inches or less of the intersection of the longitudinal axis and the bottom and sized to allow the insertion of a pipette.

5. The container of claim 3, further comprising a filter over the port.

6. The container of claim 1, further comprising a flat filter over the opening.

7. The container of claim 1, further comprising a flat filter over the opening, the filter having an adhesive surface thereon adhered to the container.

8. The container of claim 7, further comprising a finger tab extending from a periphery of the filter.

9. The container of claim 7, further comprising a plurality of slits extending inward from the periphery of the filter.

10. The container of claim 1, wherein the baffles have an included angle of 34°.

11. The container of claim 1, wherein the baffles have an apex that curves toward the bottom in approximation to a quadrant of an ellipse where the ellipse is inclined at about 8–15°.

12. The container of claim 1, wherein the baffles have a maximum height of about 3/4 inch.

13. The container of claim 1, wherein the bottom is curved upward slightly from the corners to the intersection of the bottom with the longitudinal axis.

14. The container of claim 1, wherein a biological material and growth liquid are placed in the container to a level that is about 0.8 to 1.25 times the height of the baffles measured at the corners of the container.

15. The container of claim 1, wherein the one side of each baffle is inclined and the opposing side is substantially perpendicular.

16. The container of claim 1, wherein at least one of the baffles has a side that is concave.

17. The container of claim 1, wherein the bottom comprises a sheet of material that is deformed to define the shape of the baffle.

18. A kit for cell growth by artificial cultivation of selected biological material in a growth liquid for use in an oscillating incubator, the kit comprising:
a container having a large opening centered on a longitudinal axis, the container having a circular bottom with rounded corners joining a sidewall enclosing a usable volume, the bottom having six equally spaced baffles extending inward from the corners toward a central, longitudinal axis, the baffles extending upward toward a large diameter opening of the container that is centered on the longitudinal axis and connected to the sidewall, the baffles having a triangular cross-sectional shape with an included angle of about 28–40°, the baffles ending before the longitudinal axis and having the sides of the baffles join at an apex that curves or approximates a curve, the container and baffles being blow molded of a polymer suitable for blow molding; and a first air permeable filter sized to cover the large opening of the container.

19. The kit of claim 18, wherein the container is placed in a bag, sealed and sterilized.

20. The kit of claim 18, wherein the container and filter are each placed in a same bag, sealed and sterilized.

21. The kit of claim 18, wherein the container is placed in a first bag, sealed and sterilized and the filter is placed in a second bag, sealed and sterilized.

22. The kit of claim 18, wherein the container has a pipette access port in the sidewall, and the kit further comprises a second filter sized to cover the access port.

23. The kit of claim 18, wherein the baffles have an included angle of about 34° or less and end before the longitudinal axis a distance of about 1/6 to about 1/7 the diameter of the bottom.

24. The kit of claim 18, wherein the filter has a finger tab extending from a periphery of the filter.

25. The kit of claim 18, wherein the baffles have a height of about one inch or less and wherein the baffles curve toward the bottom in approximation to a quadrant of an ellipse where the ellipse is inclined at about 8–15° and end before the longitudinal axis at a distance of about 1/6 to 1/7 the diameter of the bottom.

26. The kit of claim 18, wherein each baffle has a leading side and an opposing side each of which is inclined about the same angle.

27. The kit of claim 18, wherein each baffle has a leading side and an opposing side one of which is substantially vertical and the other of which is inclined at an angle of about 17°.

28. The kit of claim 18, wherein the filter comprises an air permeable tape with releasable adhesive on one side of the tape.

29. A container for cell growth by artificial cultivation of selected biological material in a growth liquid for use in an oscillating incubator, comprising:
the container having a large opening centered on a longitudinal axis, the container having a circular bottom with rounded corners joining a sidewall enclosing a usable volume, the bottom having four to eight equally spaced baffles extending inward from the corners toward a central, longitudinal axis and ending before that axis at a distance of about 1/6 to 1/7 the diameter of the bottom, the baffles extending upward toward a large diameter opening of the container that is centered on the longitudinal axis and connected to the sidewall, the baffles having a triangular cross-sectional shape with a leading and trailing side each upwardly inclined and intersecting at an apex having an included angle, θ, the baffles ending before the longitudinal axis and having apex curve or approximates a curve, the container and baffles being blow molded of a polymer suitable for blow molding; and a first air permeable filter sized to cover the large opening of the container.

30. The container of claim 29, wherein the included angle θ is about 28–40°.

31. The container of claim 29, wherein the included angle θ is about 17°.

32. The container of claim 29, wherein one of the sides of a plurality of the baffles is inclined and the other side of that plurality is substantially vertical.

33. The container of claim 29, further comprising a pipette access port formed in the sidewall.

34. The container of claim 29, further comprising a pipette access port formed in the sidewall and a second filter covering that access port.

35. The container of claim 29, wherein the baffles have a height of about 0.5 inches to about one inch.

36. The container of claim 29, wherein the filter comprises a flat disk with releasable adhesive on one side of the filter.

37. The container of claim 29, wherein the filter comprises an air permeable adhesive tape.

38. A container for cell growth by artificial cultivation of selected biological material in a growth liquid, the bottle being configured for use in an oscillating incubator, comprising:

the cell growth container having a circular bottom with rounded corners joining a sidewall that is inclined at an angle toward a longitudinal axis of the container to define a usable container volume, the bottom having a diameter and having a plurality of spaced baffles extending inward from the corners toward the longitudinal axis and upward toward a large diameter opening of the container centered on the longitudinal axis, the baffles extending from the corners to within a distance of that axis that is at least ⅙ the diameter of the bottom, the plurality of baffles having first and second sides, with at least one of the first and second sides being inclined relative to a plane in which the longitudinal axis lies and inclined in an orientation to allow fluid in the flask to flow up and over the incline during oscillation, wherein the baffles end before the longitudinal axis and have distal ends that extend away from the opening to join a central portion of the bottom centered on the longitudinal axis, the central portion of the bottom being further from the opening than the adjacent ends of the baffles.

39. The container of claim 38, wherein the baffles having a height measured parallel to the longitudinal axis of about 15–25% of the usable container volume, the baffles ending before the longitudinal axis, the container and baffles being blow molded of a polymer suitable for blow molding.

40. The container of claim 38, wherein the baffles extend radially inward.

41. The container of claim 38, wherein the first face is inclined and the second face is perpendicular to the bottom.

42. The container of claim 38, wherein both the first and second faces are inclined.

43. A container for cell growth by artificial cultivation of selected biological material in a growth liquid, the bottle being configured for use in an oscillating incubator, comprising:

the cell growth container having a circular bottom with rounded corners joining a sidewall that is inclined at an angle toward a longitudinal axis of the container to define a usable container volume, the bottom having a diameter with a plurality of spaced baffles extending inward from the corner toward the longitudinal axis and upward toward a large diameter opening of the container centered on the longitudinal axis, the baffles extending from the corners to within a distance of that axis that is at least ⅙ the diameter of the bottom, the plurality of baffles having first and second sides, with at least one of the first and second sides being inclined relative to a plane in which the longitudinal axis lies and inclined in an orientation to allow fluid in the flask to flow up and over the incline during oscillation, wherein the baffles have a height measured parallel to the longitudinal axis of about 15–25% of the usable container volume, the baffles ending before the longitudinal axis, the container and baffles being blow molded of a polymer suitable for blow molding.

44. A container for cell growth by artificial cultivation of selected biological material in a growth liquid for use in an oscillating incubator, comprising:

a circular bottom on the cell growth container, the bottom having corners joining a sidewall that is inclined at an angle toward a longitudinal axis of the container to define a container volume, the bottom having baffle means for agitating the biological material and liquid during use, wherein interior ends of the baffle means end at a central portion of the bottom that is lower than the adjacent ends of the baffle means and that is centered on the longitudinal axis.

45. A container for cell growth by artificial cultivation of selected biological material in a growth liquid for use in an oscillating incubator, comprising:

a circular bottom on the cell growth container, the bottom having corners joining a sidewall that is inclined at an angle toward a longitudinal axis of the container to define a container volume, the bottom having a diameter and having baffle means for agitating the biological material and liquid during use, wherein interior ends of the baffle means and that is centered on the longitudinal axis, the baffles means extending from corners of the container to within a distance of that axis that is at least ⅙ the diameter of the bottom.

46. The container of claim 1, wherein the baffles have a length and an apex that is not straight for its entire length.

47. The container of claim 1, wherein the baffles have a length and height, and a plurality of the baffles have a height of about .5 to about 1 inches for more than half the length of the baffle.

48. The container of claim 1, wherein the baffles have a length and a plurality of the baffles have an apex which inclines at an angle to the horizontal of about 11 degrees below horizontal.

* * * * *

UNITED STATES PATENT AND TRADEMARK OFFICE
CERTIFICATE OF CORRECTION

PATENT NO.         : 7,381,559 B2
APPLICATION NO.    : 10/864219
DATED              : June 3, 2008
INVENTOR(S)        : Samuel A. Ellis and Jeffrey L Harlen Page 1 of 1

It is certified that error appears in the above-identified patent and that said Letters Patent is hereby corrected as shown below:

In Colum 44, line 27, after "growth liquid," insert -- the bottle being configured --; Column 44, line 29, before "a circular bottom" insert -- the cell growth container having -- and after "a circular bottom" delete "on the cell growth container, the bottom having" and insert -- with rounded --;
In Column 44, line 32, after "to define a" insert -- usable --; Column 44, line 32, delete "baffle means for agitating the biological material and liquid during use, wherein interior ends of the baffle means end at a central portion of the bottom that is lower than the adjacent ends of the baffle means and that is centered on the longitudinal axis" and replace it with: -- a plurality of spaced baffles extending inward from the corners toward the longitudinal axis and upward toward a large diameter opening of the container centered on the longitudinal axis, the plurality of baffles having first and second sides, with at least one of the first and second sides being inclined relative to a plane in which the longitudinal axis lies and inclined in an orientation to allow fluid in the flask to flow up and over the incline during oscillation, wherein the interior ends of the first face is inclined and the second face is perpendicular to the bottom --; Column 44, line 47, after "baffle means" insert -- end at a central portion of the bottom that is lower than the adjacent ends of the baffle means --;
Column 44, line 48, replace "baffles" with -- baffle --

Signed and Sealed this
Third Day of July, 2012

David J. Kappos
*Director of the United States Patent and Trademark Office*